(12) United States Patent
Almeida

(10) Patent No.: US 6,228,074 B1
(45) Date of Patent: May 8, 2001

(54) MULTIPLE PULSE PHOTO-EPILATOR

(76) Inventor: Stephen Almeida, P.O. Box 854, New Labanon, NY (US) 12125

(*) Notice: Subject to any disclaimer, the term of this patent is extended or adjusted under 35 U.S.C. 154(b) by 0 days.

(21) Appl. No.: 09/173,422

(22) Filed: Oct. 15, 1998

(51) Int. Cl.$^7$ ................................................. A61B 18/18
(52) U.S. Cl. ........................... 606/9; 606/2; 607/88; 607/90
(58) Field of Search ................... 606/9, 13, 15, 606/131–133, 134; 607/63–90

(56) References Cited

U.S. PATENT DOCUMENTS

| | | | |
|---|---|---|---|
| 4,388,924 | 6/1983 | Weissmann et al. | 128/303.1 |
| 5,000,752 | 3/1991 | Hoskin | 606/9 |
| 5,226,907 | 7/1993 | Tankovich | 606/133 |
| 5,425,728 | 6/1995 | Tankovich | 606/9 |
| 5,474,549 | 12/1995 | Ortiz et al. | 606/9 |
| 5,486,172 | 1/1996 | Chess | 606/20 |
| 5,595,568 | 1/1997 | Anderson | 606/9 |
| 5,628,744 * | 5/1997 | Coleman et al. | 606/12 |
| 5,630,811 * | 5/1997 | Miller | 606/9 |
| 5,632,741 * | 5/1997 | Zavislan et al. | 606/9 |
| 5,647,866 * | 7/1997 | Zaias et al. | 606/9 |
| 5,735,844 * | 4/1998 | Anderson et al. | 606/9 |
| 5,752,948 * | 5/1998 | Tankovich et al. | 606/9 |
| 5,752,949 * | 5/1998 | Tankovich et al. | 606/9 |
| 5,766,214 * | 6/1998 | Mehl, Sr. et al. | 606/9 |
| 5,849,029 * | 12/1998 | Eckhouse et al. | 607/104 |
| 5,868,732 * | 2/1999 | Waldman et al. | 606/9 |
| 5,885,274 * | 3/1999 | Fullmer et al. | 606/9 |
| 6,050,990 * | 4/2000 | Tankovich et al. | 606/9 |

* cited by examiner

Primary Examiner—Michael Peffley
Assistant Examiner—Ahmed Farah
(74) Attorney, Agent, or Firm—John C. Serio; Brown Rudnick Freed & Gesmer

(57) ABSTRACT

Method and apparatus to cause the cessation of hair growth on a specific area of the body. The area is exposed to a particular pattern of multiple wavelength light generated by flashlamps which are filled with krypton and xenon gas. These flashlamps are connected to separate power supplies to allow simultaneous, overlap, or consecutive firing. The method consists of directing the light by means of a hollow reflective light guide in contact with the skin to prevent the light from escaping. Controlling the intensity of light and the delay between pulses allows treatment to be adjusted to different skin and hair types. Skin damage is virtually eliminated by the length and characteristic shape of the individual pulse in conjunction with consecutive firing of the flashlamps which spreads the energy over a long period of time.

12 Claims, 6 Drawing Sheets

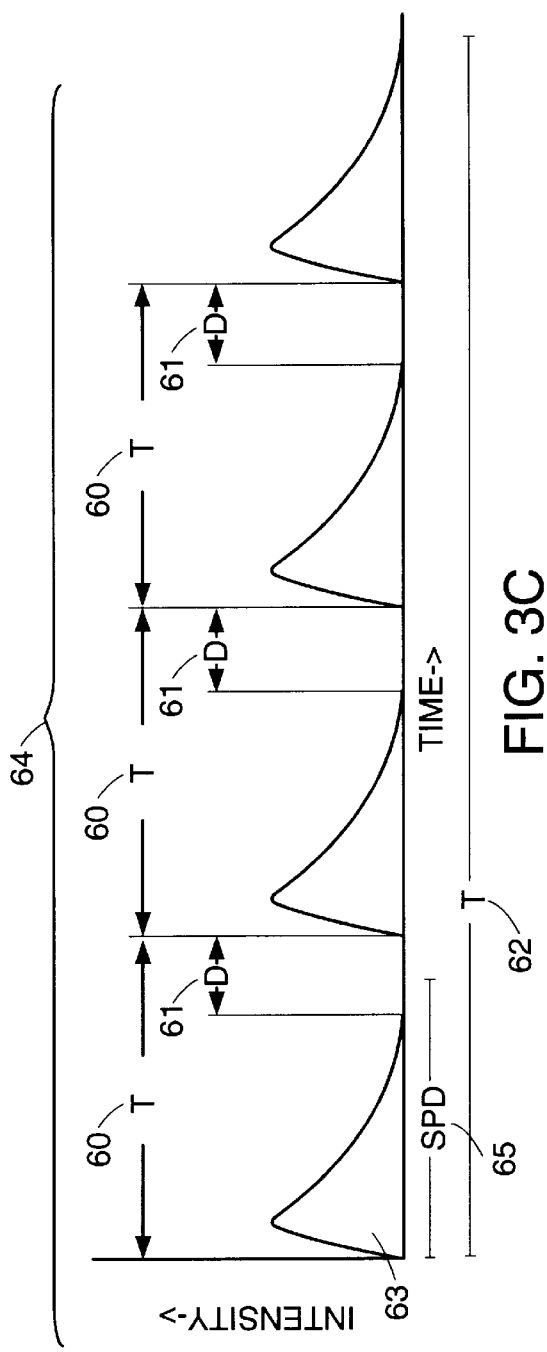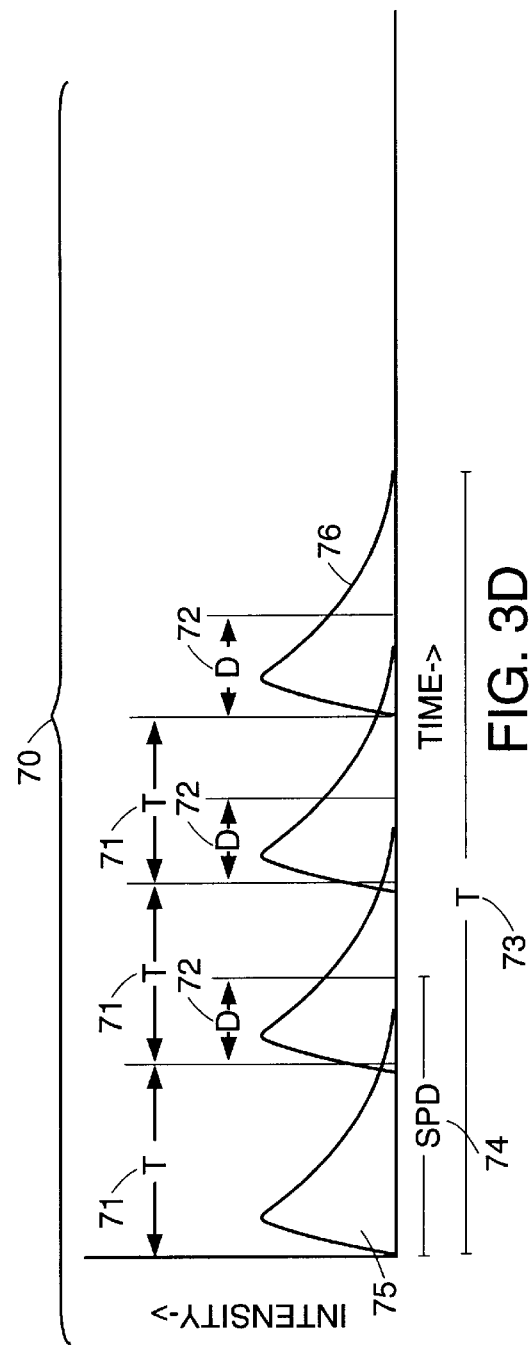

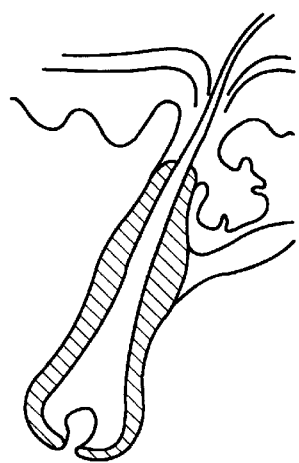
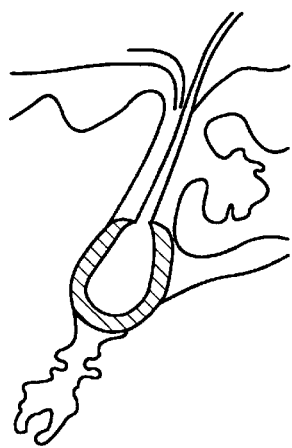
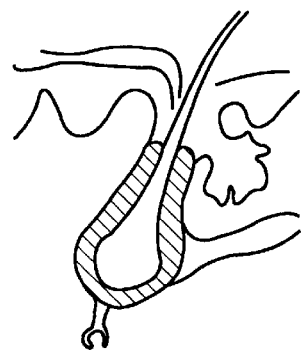
FIG. 5A    FIG. 5B    FIG. 5C
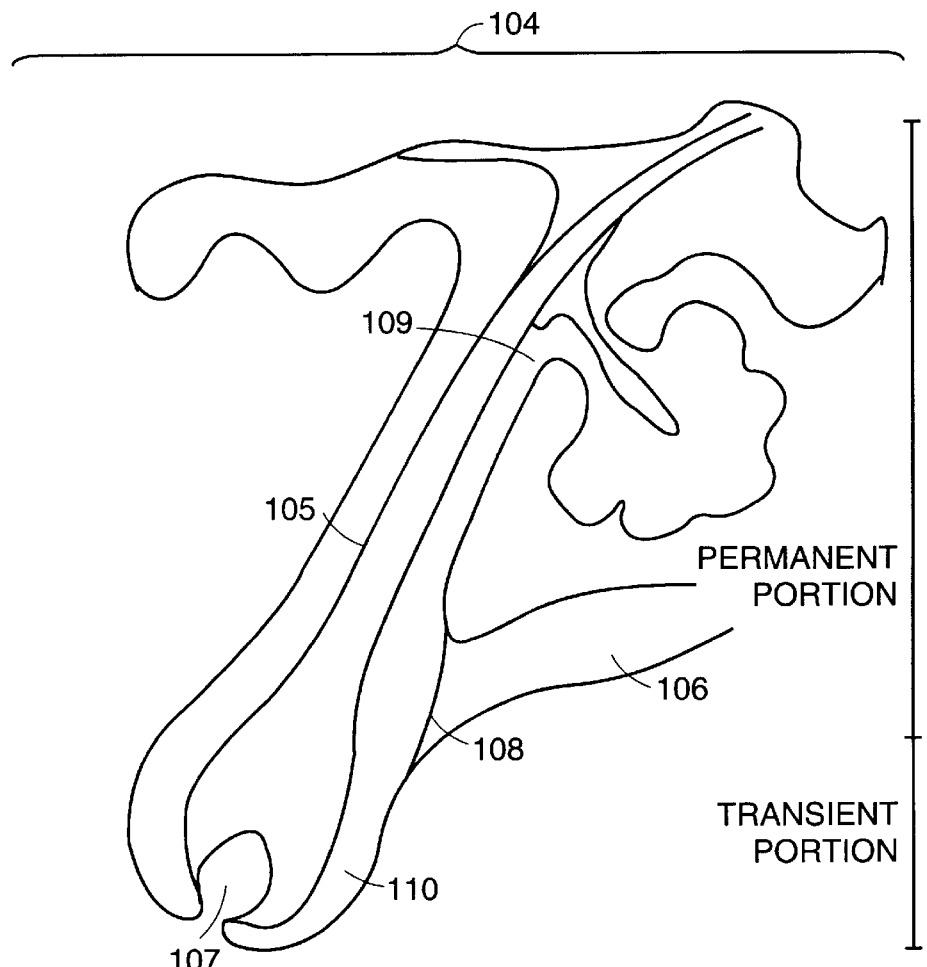
FIG. 5D

MULTIPLE PULSE PHOTO-EPILATOR

BACKGROUND

This invention relates to a painless method and device for causing temporary and/or permanent cessation of hair growth using flashlamps. Unwanted hair is an extremely common problem which can be caused by many reasons. There are many products and methods for temporarily and permanently removing hair. The methods can be very temporary such as in waxing, shaving, plucking and depilatory creams. These methods, however temporary, are very popular due to cost, quickness and/or absence of pain involved in the procedure. Electrolysis has been proven to be extremely slow and painful but is popular because of the claimed permanency and economical cost. Laser methods such as those described in U.S. Pat. No. 5,226,907 which uses a light absorbing cream in contact with the hair to create heat and destroy the hair have been shown to be painful and mostly temporary. Other laser treatments such as those stated in U.S. Pat. No. 5,595,568 use laser generated optical pulses directed through a transparent contact device which are absorbed by melanin in the hair follicle which consequently heats the hair follicle and permanently removes it. This method is effective but can be very painful since the high temperature necessary to destroy the hair follicle also destroys some surrounding tissue and skin which can result in hyper-pigmentation, blistering and possible scarring.

SUMMARY OF THE INVENTION

One embodiment of this invention sets forth a method to cause cessation of hair growth of multiple hair follicles from a selected area of the skin in an efficient and painless manner. The method consists of delivering a specific pattern of non-laser generated multiple light wavelengths which pass through the skin and into the hair and its components. The absorption of these various wavelengths results in thermal and photochemical damage to the hair and its components during the hair's Anagen phase which causes the primary effect of cessation of hair growth. While some treated areas will regenerate some regrowth, additional treatments will alleviate this residual hair growth. The multiple wavelengths that are utilized in this treatment occur at different intensities throughout the wavelength spectrum of 610 nm to 100 nm to produce a pattern that achieves optimal depth penetration. The multiple wavelength spectrum is produced by four flashlamps consisting of a specific mixture of krypton and xenon gas encased by a cerium doped synthetically fused quartz envelope. The four flashlamps are connected to separate user intensity controlled power supplies which is specifically designed to produce an 18 ms pulse duration with a specific pulse discharge pattern to accommodate different size hair follicles. Electrical supply energies of 160–400 joules are input to the flashlamps per cm2 of output. Each flashlamp can be fired simultaneously with an overlap or with a time duration of up to 40 ms between each pulse. The four flashlamps form a pulse train of four individual pulses which results in a treatment shot. Each treatment shot is separated by a 3 second interval to allow the user to move the delivery system to another area of the body for subsequent treatment. The pulse length and characteristic shape of each individual pulse is designed to distribute the energy over a time frame that virtually eliminates damage to the skin which can occur in prior methods. This method also allows the adjustment of intensity of the light source and delay between each individual pulse allowing the user to adjust to different skin and hair types.

The flashlamps utilized in the present invention are housed in a copper/zinc head which is connected to a hollow internally reflective rectangular light guide by means of a 610 nm high pass filter. The rim of the light guide is pressed against the skin so as to form an optical seal. The non-collimated light consisting of wavelengths greater than 610 nm passes through the 610 nm high pass filter and reflects at infinite angles down the hollow light guide into the skin area reaching the hair and its components.

DRAWINGS

Figure 3A:
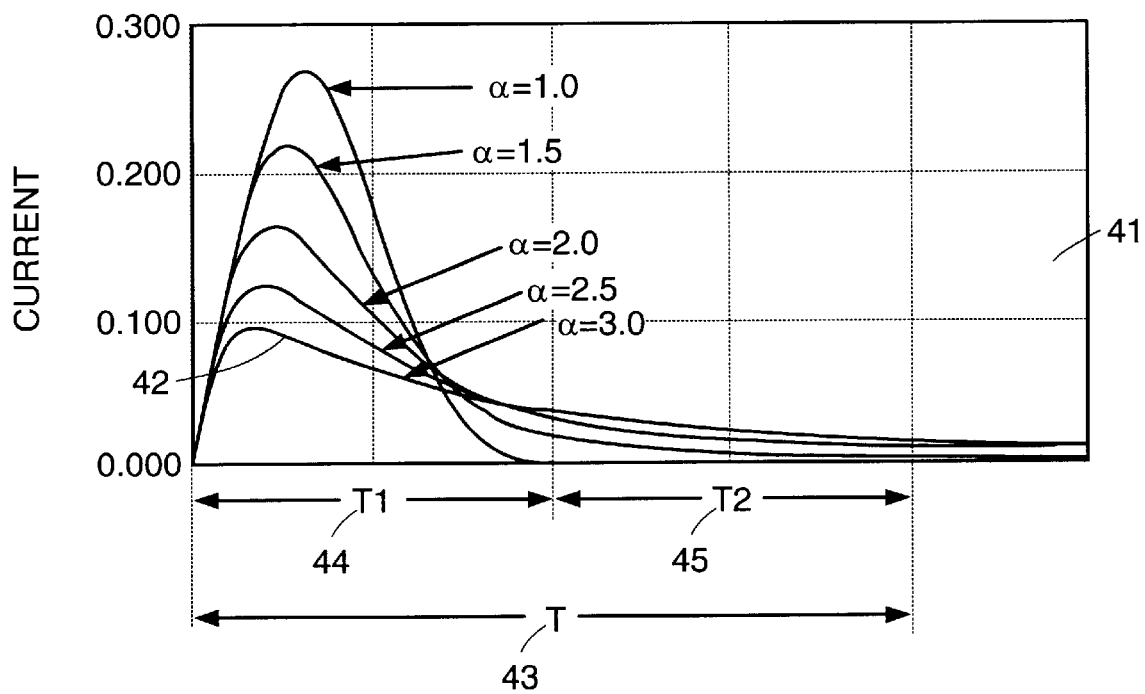
Figure 3B:
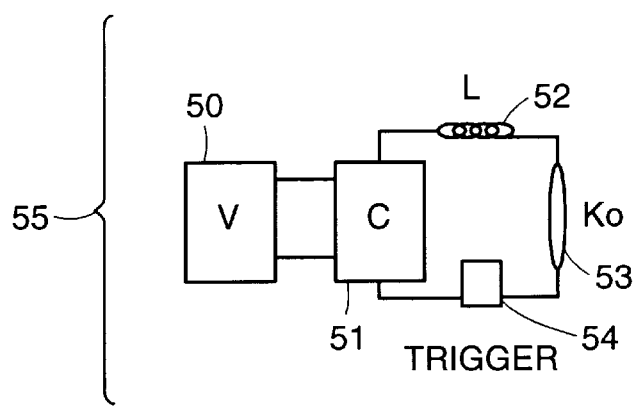

FIG. 3A shows the manipulated pulse geometry of the invention. FIG. 3B shows basic circuit components to adjust pulse geometry. FIG. 3C shows the quad pulse train of each treatment shot and the controlled delay between each pulse. FIG. 3D shows the quad pulse train of each treatment shot with a negative delay that signifies overlap.

Figure 4A:
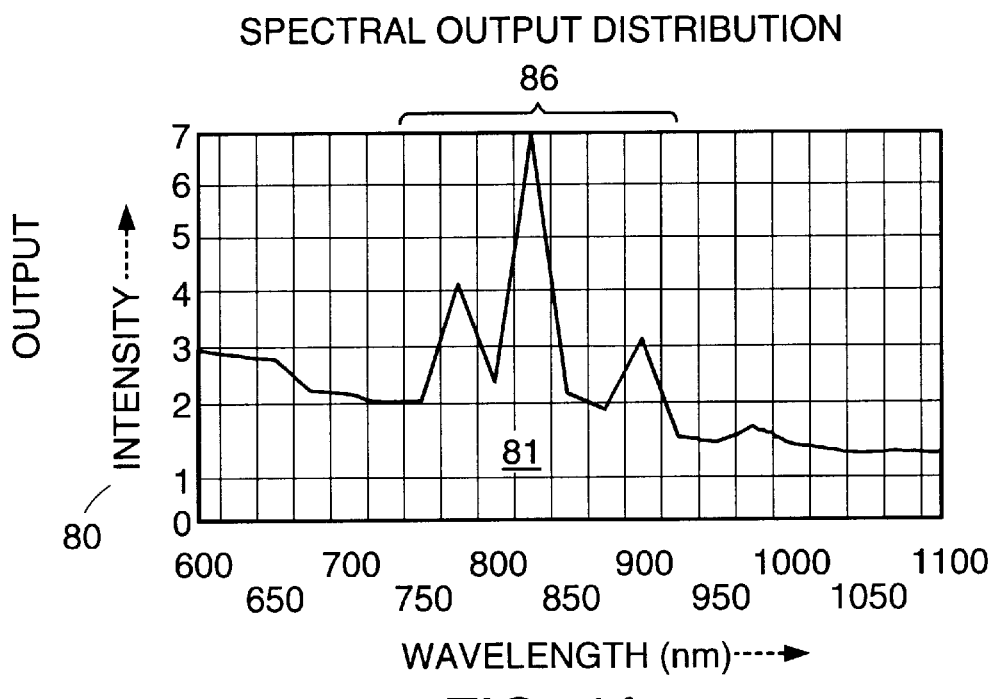
Figure 4B:
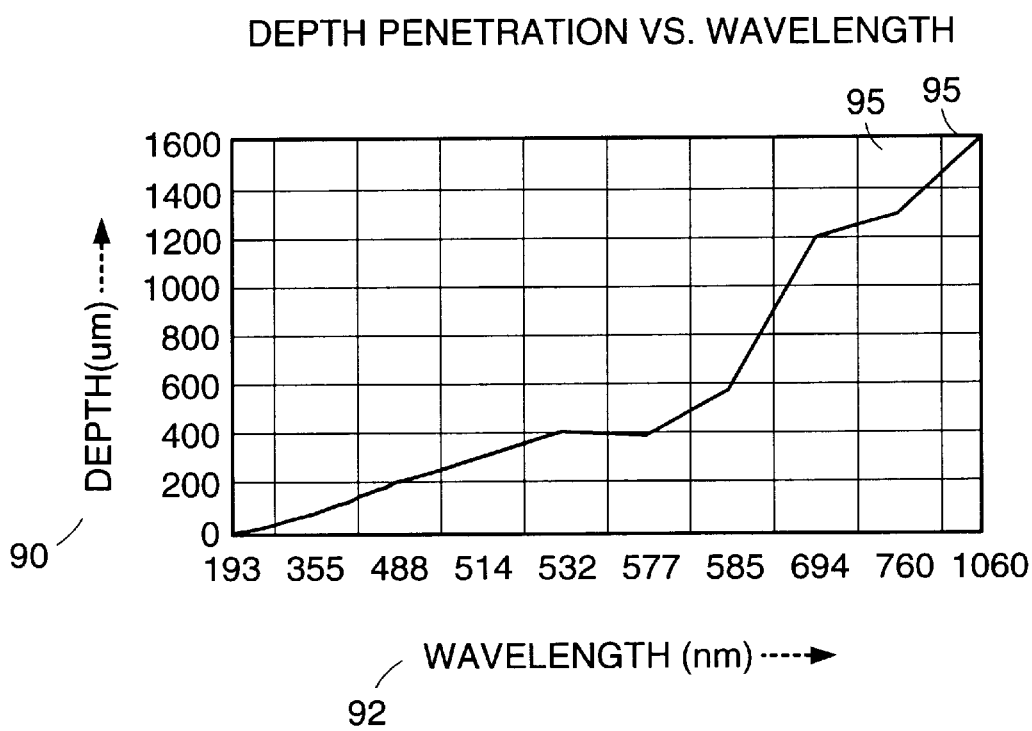

FIG. 4A is the pattern of wavelengths generated by the invention. FIG. 4B is a chart representing the depth penetration of light with respect to wavelength.

FIGS. 5A, 5B, 5C shows the cross sectional view of the different growth stages of a hair and its components. FIG. 5D shows a cross-sectional view of a hair and its components.

DETAILED DESCRIPTION

Figure 1:
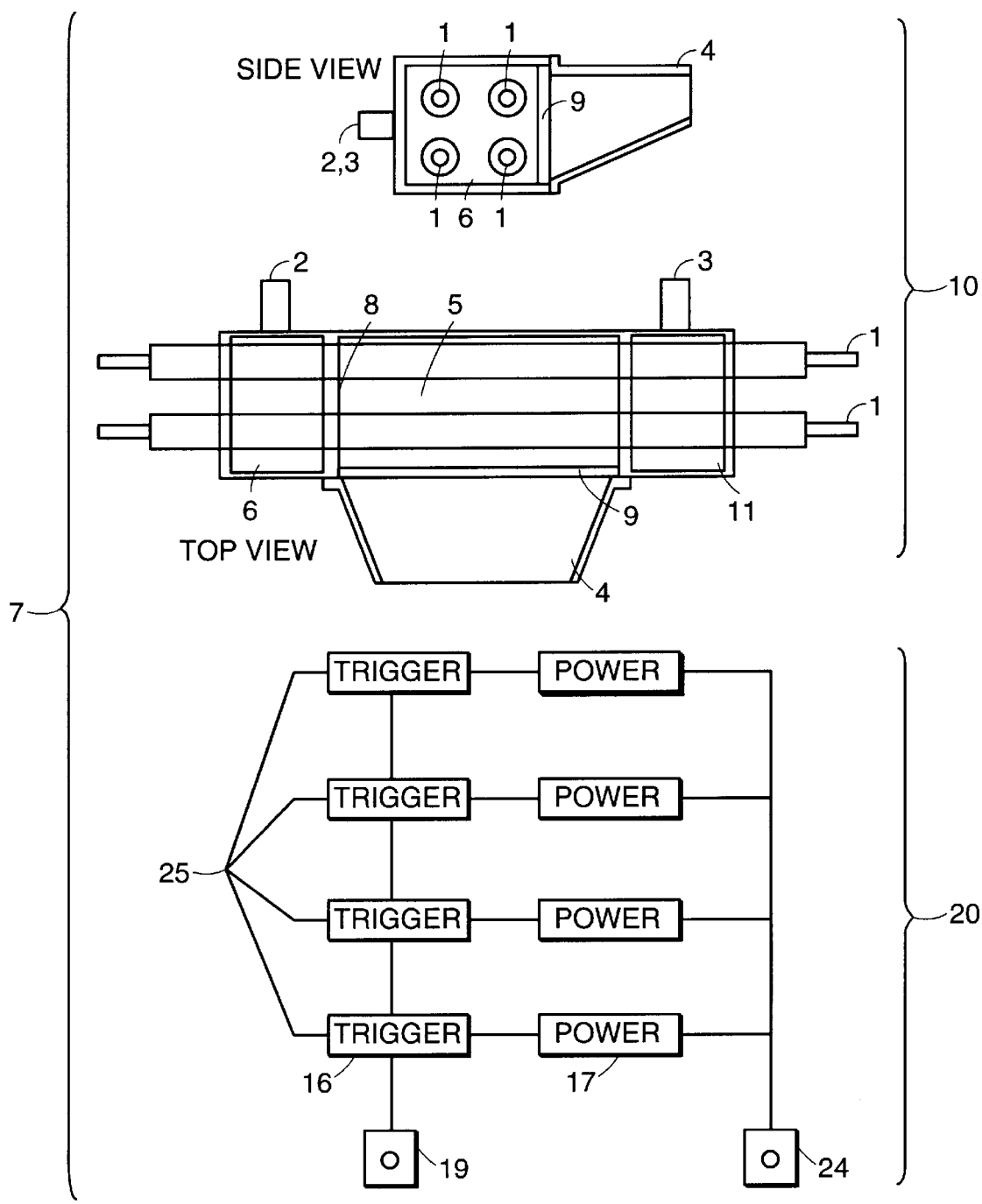
FIG. 1 is a cross sectional view of the delivery head of the device which generates and delivers the multiple wavelengths to the hair and its components and a block diagram of the power supplies and controlling electronics which control the lamps in the delivery head.

Referring to FIG. 1, a flashlamp apparatus 7 consisting of a water cooled delivery head 10 and a multiple power source capable of timed firing 20 for causing cessation of hair growth on the body. The head 10 of the apparatus contains four flashlamps 1 each containing a combination of 90% krypton gas and 10% xenon gas. When charged the combination of gases emits a specific pattern of wavelengths. This combination of gases emit a specific pattern of wavelengths which are shown in FIG. 4A. The properties of this combination of gases also lowers the required triggering voltage of the flashlamps 1. The container material of the flashlamps 1 is comprised of synthetic quartz to eliminate impurities. The use of synthetic quartz prevents the degradation of the lamp after prolonged use. Additionally, the synthetic quartz is doped with cerium in order to block diffusion of ultraviolet light under 400 nm from the lamp and thereby maintaining the integrity of the reflective chamber 5 and the 610 nm high pass filter 9. The cerium doping also has the ability to convert ultraviolet light, which would normally become waste heat, into higher wavelengths which can pass through the high pass filter 9 to create a more efficient conversion of electrical energy to light output.

The reflective chamber 5 is made of a metallic material whose reflectivity coincides with the desired output of wavelengths greater than 610 nm. In one embodiment of the invention copper reflects over 95% at 620 nm and higher wavelengths while reflecting approximately 60% at lower wavelengths. Since the desired wavelength output is greater than 610 nm, this reflectivity of copper partially absorbs the lower wavelengths in the reflective chamber 5 so the high pass filter 9 does not bear the full absorption of the lower wavelengths which would result in damage to the filter. Other reflectors such as gold and brass and even ceramic could also be used in place of copper. The delivery head 10 is cooled by water which flows in through nipple 2 and fills chamber 6, the water then flows over the lamps into the reflective chamber 5 then into chamber 11 and out nipple 3. The water which flows through delivery head 10 is recycled in a closed system through a radiator and fan assembly which uses room air as the heat exchange. The cooling system should maintain water temperatures surrounding the flashlamps 1 below a maximum continuous operating temperature of 100 degrees Celsius. Since the electrodes of flashiamps 1 create the greatest heat, chambers 6 and 11 allow a greater volume of water over these areas. An optically transparent epoxy coating 8 is used to coat the metallic reflector to prevent oxidation and degradation from the water cooling which flows from 2 to 3.

The commercially available high pass filter 9 is an optical filter which transmits only wavelengths above 610 nm. Any lower wavelengths are absorbed and converted to heat. The water in the reflective chamber 5 is also in contact with high pass filter 9 to extract the heat due to the lower wavelength absorption. This high pass filter 9 allows only wavelengths above 610 nm to enter into the hollow reflective light guide 4. The hollow reflective lightguide will be discussed in more detail in FIG. 2.

The power source and firing apparatus 20 is connected to the delivery head 10. The flashlamps 1 are connected to the switch controls 25. Each flashlamp 1 is connected to its own power supply 17. Each power supply 17 should supply 40 to 100 joules of electrical energy to each flashlamp of every cm2 of output. A firing sequence control 19 is used to activate the trigger 16 for each lamp in a simultaneous or consecutive order. Output intensity control 24 regulates the electrical energy of the power supplies 17 which discharge through the flashlamps 1. The firing sequence control 19 regulates the amount of time it takes for the output energy of one treatment shot to be dispersed while the output intensity control 24 regulates the amount of energy.

Figure 2:
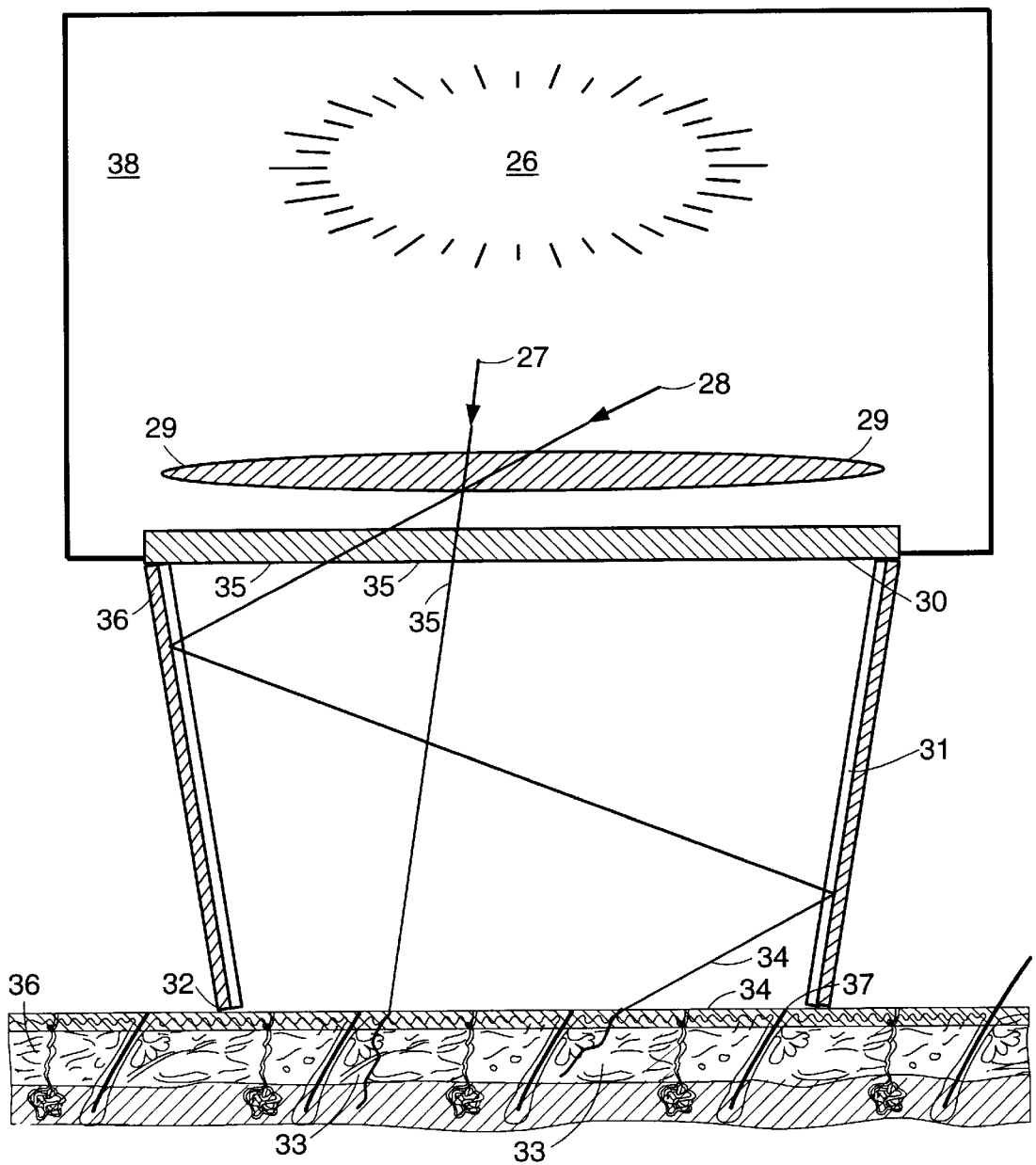
FIG. 2 is a cross sectional view of the hollow reflective light guide which guides the photons to the target area of the skin.

Referring to FIG. 2 the hollow reflective light guide shown in FIG. 1, 4. The light source from the flashlamps 26 passes through the flashlamp cooling water 29 and is represented here by individual photons 27, 28. Since the light source 26 is non-laser, and radially emitted, the light 27, 28 is reflected from the reflective chamber 38 and exits through the 610 nm high pass filter 30 (assuming the wavelength is higher than 610 nm), at multiple angles 35 down the reflective light guide 36 and into the skin at multiple angles 34 reaching the hair and its components 36 after scattering through the skin 33. The hollow reflective light guide 36 which is made of a metallic or ceramic highly reflective material for wavelengths above 610 nm is coated with an optically transparent epoxy 31 to prevent oxidation and damage to the reflective material. The light guide is pressed against the skin 32 so as to form an optical seal so no light can escape outside the light guide. This ensures all energy is transmitted through the skin and into the hair and its components. The hair is to be trimmed or shaved 37 prior to treatment so as to have no hair above the skin to absorb the light and block transmission into the skin.

Referring to FIGS. 3A and 3B which sets forth the pulse geometry and the pulse train sequence. FIG. 3A shows the formula for damping factors 40 that create various pulse geometry's shown in graph 41. The desired pulse geometry that provides the most efficacious results for cessation of hair growth is damping factor of three (3) which provides an elongated pulse 42. This geometry is the most effective for two reasons. Both reasons take advantage of the difference in thermal relaxation times of hair and skin. Thermal relaxation time is the time it takes for a body of particular size, shape, and material to dissipate 50% of its heat energy. The physical law is represented by equation 46 where d is the diameter of the body, g is the geometric factor, and k is the thermal diffusivity factor of the material. The first reason for using this specific pulse geometry is that it spreads the energy more evenly throughout the pulse length T 43 which is approximately 18 ms for the device. Since the thermal relaxation time of skin is approximately 10 ms, having the pulse duration over 10 ms prevents damage to the skin by allowing the skin to dissipate the energy and avoid being heated to high temperatures. The second reason for this pulse geometry is to take advantage of the thermal relaxation time of hair follicles. Since hair follicle sizes vary in any particular area of the body, so does their thermal relaxation times. The optimum pulse duration and geometry would be one that can be effective on the broad sizes of hair follicles while sparing the surrounding tissue. The average size hair follicles vary in thermal relaxation times from 20 ms to 100 ms. By using this specific pulse geometry, optimum damage is confined to the hair follicle for large and small hair follicles. Small follicles having a thermal relaxation time of 20 ms would dissipate the heat into the surrounding tissue rapidly resulting in a lower peak temperature in the hair follicle and creating high temperatures in the tissue. By using this specific pulse geometry 42, greater than 70% of the energy is delivered in the first half of the pulse T1 44 while the remaining energy is dispersed in the second half of the pulse T2 45. This still allows adequate cooling time for the skin but now creates higher temperatures in the small hair follicles since most of the energy is delivered in a short amount of time not allowing the follicle time to disperse the energy to the surrounding tissue. Large hair follicles having higher thermal relaxation times up to 100 ms are also effected since even more time is required to disperse the energy.

Referring to FIG. 3B the flashlamp circuit 55 necessary to accomplish this pulse geometry. The voltage supply 50 charges up the capacitor 51. When a trigger voltage is applied at 54 the flashlamp 53 ionizes allowing the power from capacitor 51 to pass through the inductor 52 and into the lamp 53 which has a certain resistance known as Ko. The values of the components in the circuit 55 must provide a damping factor of three (3) when inserted into formula 40 and also provide a pulse duration T, FIG. 3A, 43 of 18 ms.

Referring to FIG. 3C which sets forth a treatment shot from the apparatus when the treatment shot is set for consecutive firing with delays between each pulse. The treatment shot consists of a four pulse sequence train with a time delay between each pulse 64. A single pulse 63 is fired from the apparatus with time delay of T 60 before the next consecutive pulse in four pulse train is triggered. If T 60 is greater than the single pulse duration (SPD) 65 which is approximately 18 ms, then a delay D 61 is created between each pulse. This delay 61 between each pulse allows the skin to cool before the next consecutive pulse is triggered. The total time it takes the apparatus to deliver the energy is T 62 which is the combination on all the delays 61 and all the SPDs 64. This time T 62 is the duration of the treatment shot. Each treatment shot is separated by a three second interval to allow the user to move the delivery head to the next consecutive area for treatment.

Referring to FIG. 3D which sets forth a treatment shot from the apparatus when the treatment shot is set for overlap firing. The treatment shot consists of an overlap of single pulses in the four pulse train 70. Since the flashlamps are connected to separate power supplies, the apparatus is capable of overlapping pulses. If a single pulse is fired from the apparatus 75 with a consecutive triggering time delay T 71 which is shorter than the SPD 74, then a negative delay (−)D 72 is created which represents an overlap of the consecutive pulses. This overlap transforms the four single pulses into a single sawtooth appearing pulse 76 of duration T 73. This single sawtooth pulse 76 will allow more energy in a shorter amount of time T 73 than a single lamp system not capable of overlap. This higher energy in a shorter amount of time will provide more options of treatment.

Referring to FIGS. 4A and 4B which shows the spectral output patterns and depth penetration of the light generated by device. FIG. 4A refers to the graph of the output intensity 80 of the different wavelengths 81 generated by the device. The majority of the light output is in the 725 nm to 925 nm wavelengths 86 shown on the graph as the three peaks.

Referring to FIG. 4B which shows the penetration depth 90 of light versus its wavelength 92. Since the hair follicle and its components are located deep in the dermis, depth penetration of the incident light is very important. The flashlamps output was designed to generate a large amount of deep penetrating wavelengths. The peak output wavelengths of the flashlamps 95 show very good depth penetration to reach the target hair and its components.

Referring to FIGS. 5A, 5B, 5C and 5D which show the three stages of hair growth and the hair's components. All hair goes through a three stage cycle. FIG. 5A shows the growth stage (Anagen phase) of a hair and its components. This is when the hair is actively growing. FIG. 5B is the transition phase (Catagen phase) when growth slows down. FIG. 5C shows the resting stage (Telogen phase) when the hair and its components are no longer active and growing. The device is most effective during the Anagen phase FIG. 5A. It is believed that the absorption of light is greater at this time due to the enlargement of the hair components. This device has a greater effectiveness on hair during its Anagen phase, therefore, each treatment will cause cessation of hair growth on the hairs in this phase.

Referring to FIG. 5D which shows the hair and its components. The light output of the device 104 is represented here by individual photons 105–110. These photons 105–110 penetrate through the skin and into the hair and its various components labeled in the diagram. The result of the photon absorption causes thermal and photochemical damage throughout the hair and its components resulting in cessation of hair growth.

OTHER EMBODIMENTS

Other embodiments are within the scope of the following claims. For example, the pulse train may consist of three pulses instead of four and the lamps may be placed in different geometric arrangements inside the head. In addition, the ratio and amount of krypton and xenon in the flashlamps may be altered to produce a slightly different wavelength output pattern.

What is claimed:

1. A method for causing cessation of hair growth, from a section of human skin comprising the steps of:
    (a) shaving or trimming said hair in a specified skin section to be treated so that no hair growth is observable above the outer layer of said skin section;
    (b) placing a hollow reflective light guide against the skin forming an optical seal to contain a light source;
    (c) illuminating said skin section by directing said light source through a light filter and through said hollow light guide;
    (d) directing said light through said hollow light guide in a specific pulse geometry allowing a thermal relaxation time which prevents damage to said skin section.

2. The method of claim 1, wherein said pulse geometry is effective on a broad size of hair folicles.

3. The method of claim 1, wherein said light exiting said hollow light guide has a wavelength greater than 610 nm.

4. The method of claim 1, wherein said light source comprises four individual flashlamps which are fired simultaneously or consecutively with a delay between each said pulse.

5. The method of claim 4, wherein said pulses from the flashlamp are approximately 18 ms in duration with a capacitor and inductor value in the circuit to produce the geometric pulse shape described herein.

6. The method of claim 1, wherein said flashlamps are powered by electrical supply energy that is 160–400 joules for every cm2 of output.

7. The method of claim 1, wherein said light source comprises:
    a power source;
    a plurality of flashlamps;
    a water cooling system;
    a control source for firing said flashlamps.

8. The method of claim 7, wherein said control source allows simultaneous, overlap and consecutive firing of the said flashlamps.

9. The method of claim 7, wherein said flashlamps consist of synthetically fused quartz doped with cerium.

10. The method as described in claim 7 wherein said flashlamps consist of Kr, Xe gas.

11. The method of claim 1, wherein said light filter blocks wavelengths below 610 nm.

12. The method of claim 1 wherein said light spectral output pattern is generated in an output between 610 nm and 1,100 nm.

* * * * *